United States Patent [19]
Kauhaniemi et al.

[11] Patent Number: 5,880,829
[45] Date of Patent: Mar. 9, 1999

[54] APPARATUS FOR TAKING AND ANALYSING LIQUID SAMPLES, SUCH AS BLOOD SAMPLES

[75] Inventors: Ilpo Kauhaniemi, Vantaa; Pekka Heinonen; Harri Okkonen, both of Espoo, all of Finland

[73] Assignee: Nokia Mobile Phones Limited, Espoo, Finland

[21] Appl. No.: 920,045

[22] Filed: Aug. 28, 1997

[30] Foreign Application Priority Data

Sep. 2, 1996 [FI] Finland ........................ 963410

[51] Int. Cl.$^6$ ........................ G01N 1/10
[52] U.S. Cl. ........................ 356/246; 356/445
[58] Field of Search ........................ 356/244, 246, 356/39, 445; 422/58–60; 706/820

[56] References Cited

U.S. PATENT DOCUMENTS

| | | | |
|---|---|---|---|
| 4,142,863 | 3/1979 | Convington et al | 422/57 |
| 4,218,421 | 8/1980 | Mack, Jr. et al. | 422/56 |
| 4,328,184 | 5/1982 | Kondo | 422/58 |
| 5,413,761 | 5/1995 | Dulaney | 422/56 |
| 5,424,035 | 6/1995 | Hones et al. | 422/55 |
| 5,609,823 | 3/1997 | Harttig et al. | 422/58 |
| 5,679,311 | 10/1997 | Harrig et al. | 422/58 |
| 5,720,924 | 2/1998 | Eikmeier et al. | 422/102 |

FOREIGN PATENT DOCUMENTS

| | | |
|---|---|---|
| 0 199 484 | 10/1986 | European Pat. Off. . |
| 42 34 553 | 4/1993 | Germany . |
| 86/00513 | 1/1986 | WIPO . |

*Primary Examiner*—Robert Kim
*Attorney, Agent, or Firm*—Perman & Green, LLP

[57] ABSTRACT

The invention relates to an apparatus for taking and analysing liquid samples, such as blood samples, wherein a liquid, absorbed by a porous material, is analysed optically. The apparatus, according to the invention, comprises a store (2) for measurement strips that receive samples and have been interconnected so that they can be disconnected, the store having a compound construction, a measurement strip feeding mechanism (3) and a blood analyzer (4). The apparatus has preferably been integrated into a casing (1), which can be connected as part of a mobile telephone or a corresponding device.

13 Claims, 3 Drawing Sheets

APPARATUS FOR TAKING AND ANALYSING LIQUID SAMPLES, SUCH AS BLOOD SAMPLES

FIELD OF THE INVENTION

The object of the present invention is an apparatus for taking and analysing samples, such as blood samples, wherein a liquid, absorbed by a porous material, is analysed optically.

The invention relates particularly to the repeated control of the quality of a patient's blood, e.g., to the control of the glucose content of the blood of a diabetic patient or to the measuring of the blood's cholesterol content, which can be defined optically on the basis of the colour of a transilluminating or reflecting ray of light.

BACKGROUND OF THE INVENTION

Different types of apparatuses are known that make blood analyses swiftly and reliably. For example, the skin is lanced with a small, spring-mounted lancet, and the drop of blood from the skin is absorbed into a small, gauze dressing-like pad. The gauze dressing is normally attached to the centre of a narrow piece of plastic forming a so-called strip.

In the plastic strip, there is a hole covered with a transparent or coloured film that penetrates light, whereto light is directed. By using a suitable strip and a calculation model, it is possible to define accurately, on the basis of the reflected colour, the blood property controlled at the time, e.g., the glucose or cholesterol content.

A disadvantage of the apparatuses in question, particularly in long-term use, is that the measurements must be taken where the apparatuses are located, i.e., at home, at a workplace or at the doctor's. For example, for a diabetic, who has accurate medication times directly dependent on the glucose content of the blood, this is an impediment to a freedom of movement and living.

A glucose pen is disclosed in publication DE 4234553 which incorporates a store of test strips having separate test strips lying next to each other in an inclined position. The test strips can be removed at one end of the store through cylinders by rolling one of the cylinders. The remaining test strips are kept at the removal end by a spring force pushing the test strips in direction of the removal opening. The glucose pen also incorporates a lancet and a color scale.

SUMMARY OF THE INVENTION

The object of the present invention is to produce an apparatus for taking and analysing samples that a user can carry with him and easily use wherever he goes. It is characteristic of the apparatus, according to the invention, that it comprises a store for measurement strips that receive samples and are bound together in a folding manner, the store having a compound construction, of a measurement strip feeding mechanism and of blood analysing means.

The apparatus, according to the present invention, has many advantages. The handling of individual strips ends and it is possible to place, in the store of the apparatus, a number of strips equivalent to at least one week's need, depending on the case and as necessary. A user of the apparatus can carry it with him and use it wherever he goes, i.e., the user no longer has to go to a specific place for a test.

It is characteristic of a preferred embodiment of the present invention that the apparatus includes a lancet for taking a blood sample. The lancet, with its setting and releasing mechanism, can also be included in .the apparatus as its fixed part, whereupon the whole act of testing is as easy and unnoticeable as possible. Preferably, the apparatus has an in-built display for displaying the results of the analyses.

It is also characteristic of a preferred embodiment of the present invention that the apparatus has been integrated into a casing, which can be connected as part of a mobile telephone or a corresponding device. This can be implemented either so that the apparatus contains batteries of the mobile telephone and it has been formed to replace the mobile telephone's battery packet or so that the apparatus has been formed to be connected on top of the mobile telephone's battery packet. In both cases, a user of the apparatus, according to the present invention, can easily carry it with him wherever he goes.

The other preferred embodiments of the invention are characterised in what has been presented later in the claims.

BRIEF DESCRIPTION OF THE DRAWINGS

In the following, the invention will be discussed in detail with the help of examples by referring to the enclosed drawings, where.

DETAILED DESCRIPTION

Figure 1:
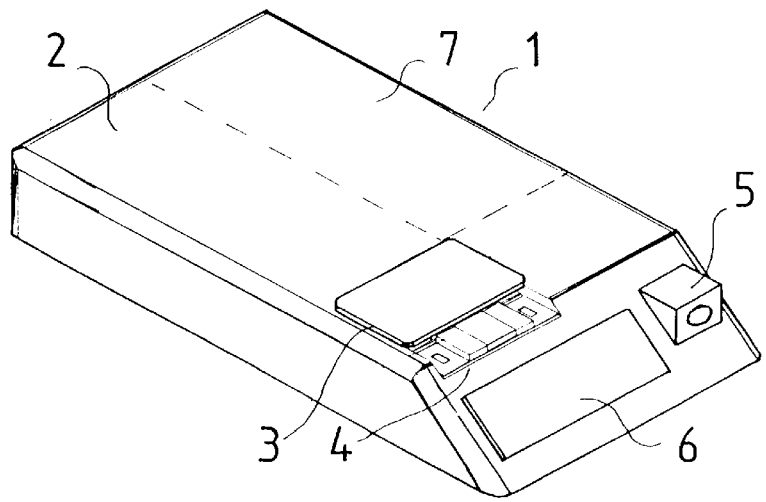
FIG. 1 illustrates a perspective of an apparatus according to the invention.

FIG. 1 illustrates a perspective of an apparatus according to the invention. All the necessary means have been integrated into a casing 1 which, thus, includes a store or a box 2 for measurement strips receiving liquid samples, interconnected foldingly, a measurement strip feeding mechanism 3, as well as a blood analysing station 4. In addition, the apparatus includes a lancet 5 for taking a blood sample, an electronic unit 7 and a display 6 for displaying the results of analyses.

Figure 2:
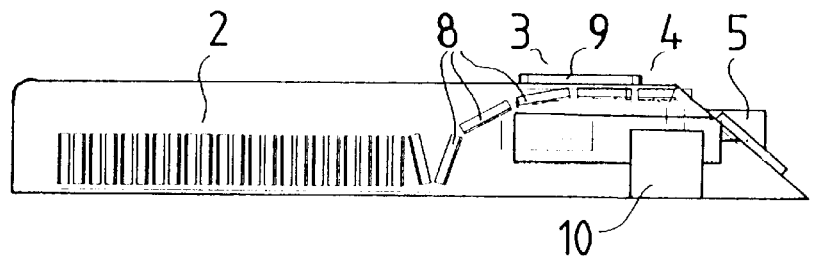
FIG. 2 illustrates an apparatus, according to FIG. 1, as a section seen from the side.

FIG. 2 illustrates an apparatus, according to the invention, as a section seen from the side, wherein folded measurement strips 8 can be distinguished inside the box 2. The measurement strips are conveyed from the box 2 to the feeding mechanism 3, a sliding plate 9 of which operates as presented below. The measurement strips 8 go one by one to the analysing station 4, which has a source of light having a standard construction and a reflected light detector 10.

Figure 3:
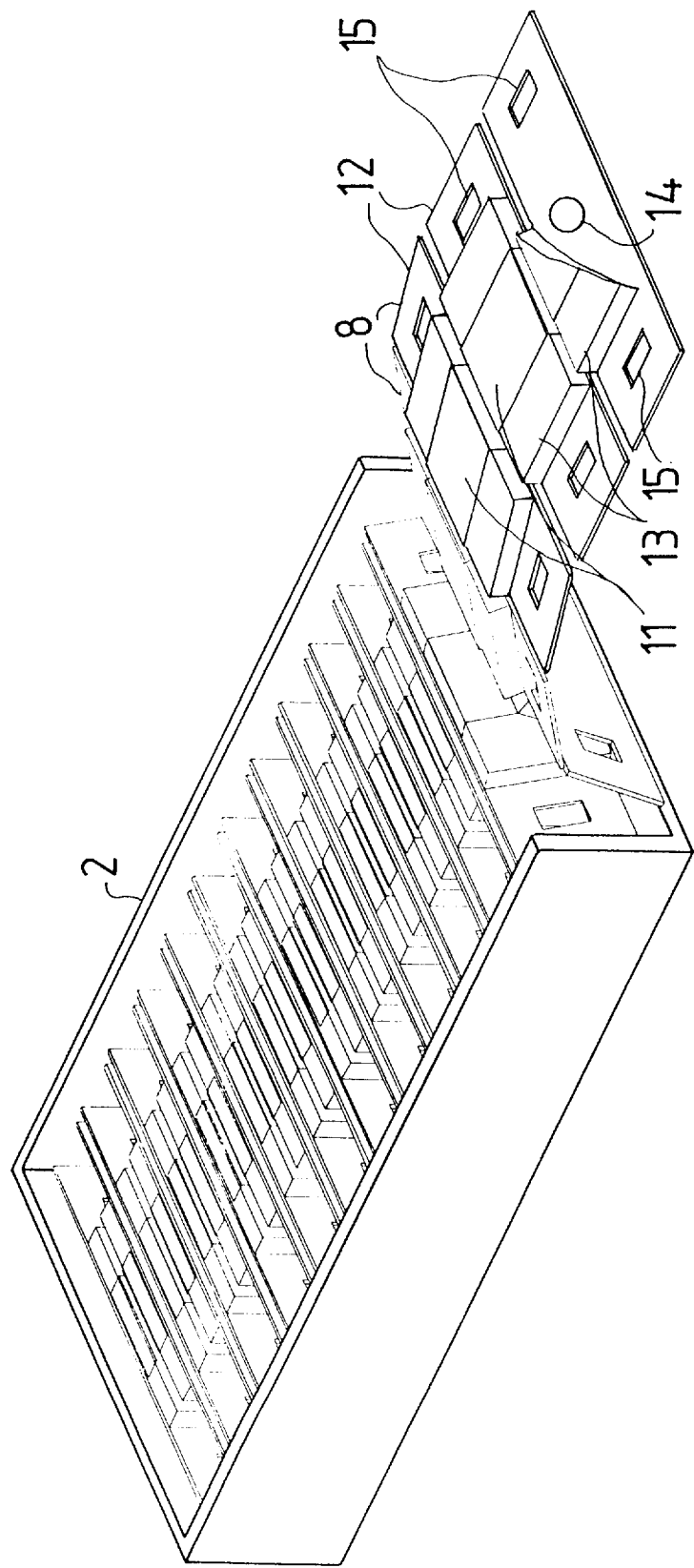
FIG. 3 illustrates a store for strips of an apparatus, according to the invention, and its operation.

FIG. 3 illustrates, on an enlarged scale, the measurement strips 8 and the structure of their storage box in more detail: an individual measurement strip comprises a gauze dressing 11, made of an absorbent material and receiving a sample drop, which has been attached to a plastic base 12 by means of adhesive pads 13 or corresponding fixing elements. It can be seen in the first, partly cut measurement strip that, in the middle of the base 12, there is a hole 14, which has been covered with a colourless or coloured film, i.e., a filter, in order to produce a reflecting ray of light of a required colour for the detector. Alternatively, the filter can be connected as part of the gauze dressing as its base layer.

There are also other holes 15 at the ends of the measurement strips, the function of which will be described later. The individual measurement strips have been bound together by adhesive tape or corresponding means, or they are of the same piece perforated in between. The binding between the measurement strips enables the strips to be fed forwards as a continuous band by means of the feeding mechanism and to be folded or stored in some other space-saving manner, as well as the individual strips to be torn off after the act of measuring.

Figure 4A:
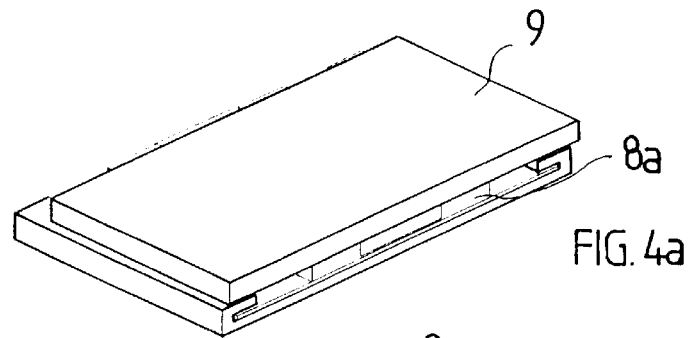
FIGS. 4a–4c illustrate the operation of a feeding mechanism of an apparatus according to the invention.
Figure 4B:
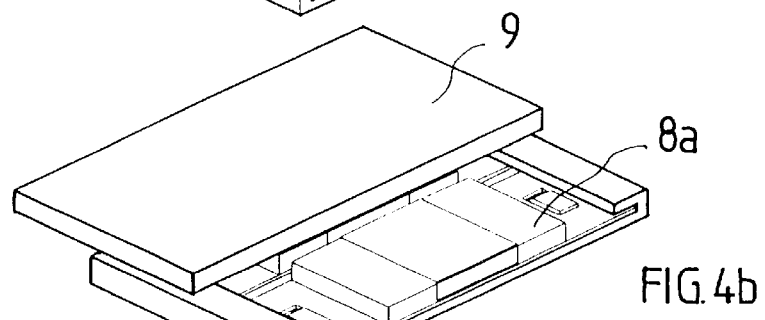
Figure 4C:
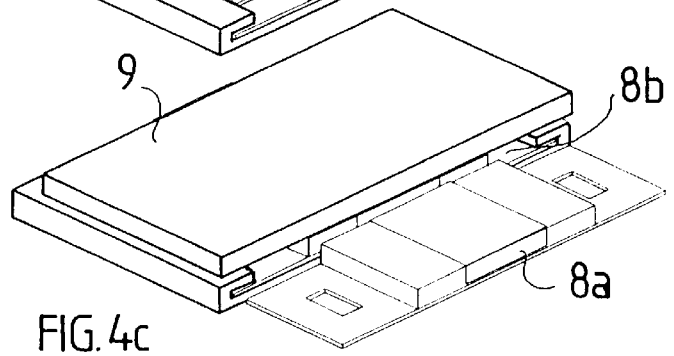

FIGS. 4a–4c illustrate the operation of the feeding mechanism 3 of an apparatus according to the invention. In FIG. 4a, the sliding plate of the feeding mechanism is in a protecting position covering a ready-to-use measurement strip 8a located on the analysing station 4. In FIG. 4b, the sliding plate 9 has been pulled to a so-called analysing position uncovering the measurement strip 8a. When the sliding plate, according to FIG. 4c, is pushed back to the protecting position after the analysis, it pushes the used measurement strip outwards and places a new strip 8b on the analysing station 4. The used strip can now be removed by cutting the tape that binds the strips together, e.g., against a sharp edge or by tearing along the perforations, depending on the implementation.

Figure 5:
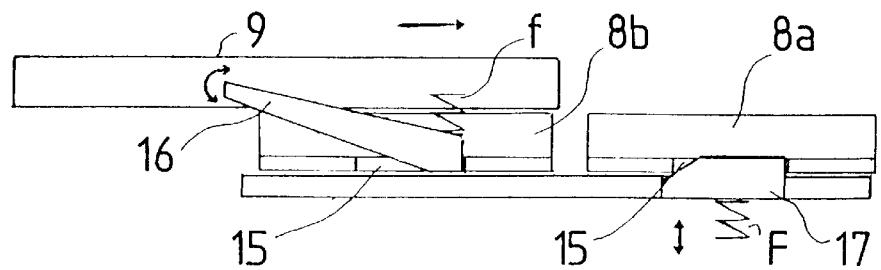
FIG. 5 illustrates a feeding mechanism as a section seen from the side.

FIG. 5 illustrates in detail the feeding mechanism of an apparatus according to the invention. The sliding plate 9 has been illustrated in an analysing position, i.e., with the foremost measurement strip 8a ready for use. The strip 8a remains in its place due to two holding elements 17 penetrating, by means of a spring, its holes 15 from below. When a drop of blood etc. has been dropped on the strip and the analysis has been made, a second measurement strip 8b pushes, on one hand, the holding elements 17, elastic in the vertical direction, downwards by pushing against their bevel back edge and, on the other hand, the strip 8a out of the apparatus, where it can be torn off. This happens automatically, when the sliding plate 9 is returned to the protecting position in the direction indicated by an arrow.

The new strip 8b is pushed forwards by spring-loaded pushing levers 16, attached to the sliding plate, which push the strip from the front edge of its holes 15. By this solution no spring force exercising a pushing force on the strips inside the store is needed, especially any force on the gauze dressing 11 is avoided. Rather the measurement strips 8 lie side by side in the store and they are pulled out of the store by the pushing levers 16. However, a spring force f of the pushing levers is weaker than a spring force F of the holding elements 17, thus, when the sliding plate is pulled back for a new analysis, the strip 8b remains in its place on top of the analysing station (cf. FIG. 4c).

Figure 6:
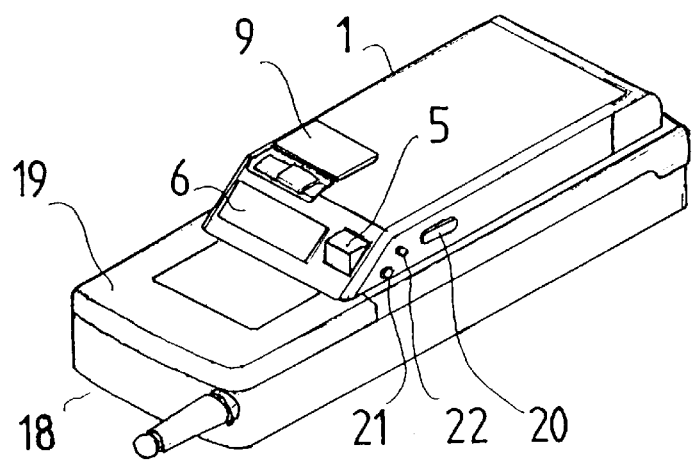
FIG. 6 illustrates an apparatus, according to the invention, connected to a mobile telephone.

FIG. 6 illustrates a case, wherein the casing 1 of an apparatus, according to the invention, has been connected as part of a mobile telephone 18 so that it locks on a battery packet 19 of the mobile telephone. It is disconnected by pushing a button 21. The spring-mounted lancet is set and released by buttons 22 and 20 in a known manner. Alternatively, the apparatus may contain in itself batteries of a mobile telephone, whereupon it replaces the mobile telephone's battery packet. In this embodiment the batteries in the apparatus supply energy both for the mobile telephone to which it is connected and to the apparatus itself, e.g. the display 6 and the analysing station 4.

The apparatus, according to the invention, is used in the case, illustrated in FIG. 6, so that the lancet is set, a finger is placed on the lancet, whereupon the lancet's needle lances the skin as the lancet is released. The sliding plate 9 is pulled to the analysing position and a drop of blood from the finger is placed on the measurement strip coming out. The analysing process is carried out either automatically or by pushing a start button (not illustrated), whereupon a source of light/a source of light located in the detector unit 10 transmits a ray of light towards the measurement strip's centre hole 14, wherefrom it is reflected back to the detector, i.e., a photosensor, located in the unit 10.

The formed electric signal is transmitted to the electronic unit 7 of the apparatus, which programmable carries out a blood analysis using methods known as such. The result of the analysis is displayed on the display 6. The apparatus is switched off by the start button or by pushing the sliding plate 9 back to the protecting position.

It is obvious to a person skilled in the art that the different embodiments of the present invention are not restricted to the examples presented above, and that the various options of implementing the invention, as determined by the claims, also belong to the scope of the invention.

We claim:

1. An apparatus for taking and analysing liquid samples wherein a liquid absorbed by a porous material is analysed optically, and wherein the apparatus has been integrated into a casing, the apparatus comprising:

a store for measurement strips having said porous material for receiving the samples, wherein the measurement strips have been interconnected disconnectably and in a foldable manner and are arranged side by side within the store, the interconnected measurement strips form a strip band, the store having a compound construction, a measurement strip feeding mechanism for taking the measurement strips from the store, the measurement strip feeding mechanism comprising means for pulling the measurement strips of said strip band out of said store, and blood analysing means for analysing the samples on the measurement strips.

2. An apparatus according to claim 1, wherein the apparatus includes a lancet for lancing the skin of a user for taking a blood sample of said user.

3. An apparatus according to claim 1, wherein the apparatus includes a display for displaying the results of the analyses.

4. An apparatus according to claim 1, wherein the measurement strip store is an elongated magazine, wherein the measurement strips have been arranged foldingly.

5. An apparatus according to claim 1, wherein the blood analysing means comprise a source of light and the required optics for detecting a ray of light reflecting off the samples as well as electronics for carrying out an analaysis.

6. An apparatus according to claim 1, wherein said casing has been adapted to be connected as part of a mobile telephone.

7. An apparatus according to claim 6, wherein said casing of the apparatus includes batteries of a mobile telephone, and the casing has been formed to replace a battery packet of the mobile telephone.

8. An apparatus according to claim 6, wherein said casing of the apparatus has been formed to be connected on top of the battery packet of the mobile telephone.

9. An apparatus according to claim 1, wherein the measurement strip feeding mechanism has been arranged to pull out the measurement strips from the store without exercising a pushing force on the measurement strips inside the store.

10. An apparatus for taking and analysing liquid samples wherein a liquid, absorbed by a porous material, is analysed optically, and wherein the apparatus has been integrated into a casing, the apparatus comprising:
- a store for measurement strips having said porous material for receiving the samples,
- a measurement strip feeding mechanism for taking the measurement strips from the store,
- blood analysing means for analysing the samples on measurement strips, and
- wherein said casing of the apparatus has been formed to be connected as part of a mobile telephone.

11. An apparatus according to claim 10 wherein said casing of the apparatus includes batteries of a mobile telephone, and the casing has been formed to replace a battery packet of the mobile telephone.

12. An apparatus according to claim 10, wherein said casing of the apparatus has been formed to be connected on top of the battery packet of the mobile telephone.

13. An apparatus according to claim 10, wherein said casing of the apparatus includes a lancet for lancing the skin of a user for taking a blood sample of said user.

* * * * *